(12) United States Patent
Breyfogle et al.

(10) Patent No.: US 8,088,364 B2
(45) Date of Patent: Jan. 3, 2012

(54) PERSONAL-CARE COMPOSITION COMPRISING OIL-SOLUBLE SOLID SUNSCREENS

(75) Inventors: Laurie Ellen Breyfogle, Milford, OH (US); Rebecca Ann Finley, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/728,183

(22) Filed: Mar. 19, 2010

(65) Prior Publication Data
US 2010/0303744 A1 Dec. 2, 2010

Related U.S. Application Data

(60) Provisional application No. 61/161,953, filed on Mar. 20, 2009.

(51) Int. Cl.
*A61K 8/00* (2006.01)
(52) U.S. Cl. .......................................................... 424/59
(58) Field of Classification Search .................. None
See application file for complete search history.

(56) References Cited

U.S. PATENT DOCUMENTS

| | | | |
|---|---|---|---|
| 2,798,053 A | 7/1957 | Brown | |
| 3,755,560 A | 8/1973 | Dickert | |
| 4,096,240 A * | 6/1978 | Mathur | 424/59 |
| 4,206,215 A | 6/1980 | Bailey | |
| 4,421,769 A | 12/1983 | Dixon | |
| 4,509,949 A | 4/1985 | Huang | |
| 4,578,266 A | 3/1986 | Tietjen | |
| 4,980,155 A | 12/1990 | Shah | |
| 5,059,414 A | 10/1991 | Dallal | |
| 5,066,485 A | 11/1991 | Brieva | |
| 5,087,445 A | 2/1992 | Haffey | |
| 5,304,334 A | 4/1994 | Lahanas | |
| 5,362,482 A | 11/1994 | Yoneyama | |
| 5,412,004 A | 5/1995 | Tachibana | |
| 5,882,657 A | 3/1999 | Miguel Colombel | |
| 5,939,082 A | 8/1999 | Oblong | |
| 5,997,887 A | 12/1999 | Ha | |
| 6,039,935 A | 3/2000 | Mohammadi | |
| 6,039,960 A | 3/2000 | Chung | |
| 6,177,091 B1 | 1/2001 | Bara | |
| 6,207,596 B1 | 3/2001 | Rourke | |
| 6,235,292 B1 | 5/2001 | Bara | |
| 6,245,344 B1 | 6/2001 | Thibiant | |
| 6,258,345 B1 | 7/2001 | Rouquet | |
| 6,280,753 B1 | 8/2001 | Chung | |
| 6,331,306 B1 | 12/2001 | Afriat | |
| 6,488,941 B1 | 12/2002 | Burnier | |
| 6,492,326 B1 | 12/2002 | Robinson | |
| 6,503,944 B1 | 1/2003 | Chanchani | |
| 6,524,598 B2 | 2/2003 | Sunkel | |
| 6,544,532 B1 | 4/2003 | Jager Lezer | |
| 6,548,050 B1 | 4/2003 | Bara | |
| 6,562,322 B2 * | 5/2003 | Brieva et al. | 424/64 |
| 6,696,049 B2 | 2/2004 | Vatter | |
| 6,905,695 B1 | 6/2005 | Afriat | |
| 2002/0037302 A1 | 3/2002 | Afriat | |
| 2003/0082219 A1 | 5/2003 | Warren | |
| 2004/0175347 A1 | 9/2004 | Bissett | |
| 2004/0176273 A1 | 9/2004 | Bissett | |
| 2004/0219124 A1 | 11/2004 | Gupta | |
| 2004/0223989 A1 | 11/2004 | Auguste | |
| 2004/0228884 A1 | 11/2004 | Gupta | |
| 2004/0234477 A1 | 11/2004 | Sakuta | |
| 2005/0019356 A1 | 1/2005 | Bissett | |
| 2005/0025727 A1 * | 2/2005 | Lott | 424/59 |
| 2005/0136012 A1 | 6/2005 | Gonzalez | |
| 2005/0142079 A1 | 6/2005 | Garrison | |
| 2005/0220728 A1 | 10/2005 | Kanji | |
| 2006/0013793 A1 | 1/2006 | Themens | |
| 2006/0074097 A1 | 4/2006 | Bissett | |
| 2006/0147508 A1 | 7/2006 | Gupta | |
| 2006/0263309 A1 | 11/2006 | Bissett | |
| 2006/0275237 A1 | 12/2006 | Bissett | |
| 2007/0128137 A1 | 6/2007 | Yoshimi | |
| 2007/0248550 A1 | 10/2007 | Patel | |
| 2007/0264210 A1 | 11/2007 | Robinson | |
| 2007/0274932 A1 | 11/2007 | Suginaka | |
| 2007/0297996 A1 | 12/2007 | Tanner | |
| 2007/0297997 A1 | 12/2007 | Tanner | |
| 2008/0038216 A1 | 2/2008 | Zukowski | |
| 2008/0038360 A1 | 2/2008 | Zukowski | |
| 2009/0003920 A1 | 1/2009 | Zukowski | |
| 2009/0011035 A1 | 1/2009 | Zukowski | |
| 2010/0092408 A1 | 4/2010 | Breyfogle | |
| 2010/0119619 A1 | 5/2010 | Griffiths-Brophy | |
| 2010/0158824 A1 | 6/2010 | Lin | |
| 2010/0172849 A1 | 7/2010 | Shaow | |
| 2010/0183525 A1 | 7/2010 | Lin | |
| 2010/0303744 A1 | 12/2010 | Breyfogle | |
| 2010/0305168 A1 | 12/2010 | Robinson | |
| 2010/0305169 A1 | 12/2010 | Robinson | |

FOREIGN PATENT DOCUMENTS

| | | |
|---|---|---|
| EP | 374332 B1 | 1/1993 |
| EP | 1166746 B1 | 7/2003 |
| EP | 1068851 B1 | 9/2004 |
| EP | 1068852 B1 | 9/2004 |
| EP | 1003460 B1 | 7/2005 |
| EP | 1473016 | 11/2006 |
| JP | 2003055141 | 2/2003 |
| WO | WO2004078157 | 9/2004 |
| WO | WO2007109282 A3 | 5/2008 |

* cited by examiner

*Primary Examiner* — Tracy Vivlemore
*Assistant Examiner* — Jennifer Berrios
(74) *Attorney, Agent, or Firm* — Eric T. Addington; Megan C. Hymore; S. Robert Chuey

(57) ABSTRACT

In one embodiment, a personal-care composition in the form of a water-in-oil emulsion comprises at least about 10% of a non-polar silicone oil; from about 0.1% to about 10% of a first oil-soluble solid sunscreen; and from about 0.1% to about 10% of a second oil-soluble solid sunscreen. The weight ratio of the first sunscreen to the second sunscreen may be from about 0.8 to about 2.0, or from about 1.0 to about 1.5. The first sunscreen may be oxybenzone. The second sunscreen may be avobenzone. The composition may further comprise a skin-care active selected from the group consisting of a vitamin $B_3$ compound, a sugar amine, a peptide, a hexamidine compound, and combinations thereof. In another embodiment, the invention relates to a method for improving the solubility of a second oil-soluble solid sunscreen in the oil phase of a water-in oil emulsion.

12 Claims, 1 Drawing Sheet

PERSONAL-CARE COMPOSITION COMPRISING OIL-SOLUBLE SOLID SUNSCREENS

CROSS REFERENCE TO RELATED APPLICATION

This application claims the benefit of Provisional Application Ser. No. 61/161,953, filed Mar. 20, 2009.

FIELD OF THE INVENTION

The present invention relates to a personal-care composition in the form of a water-in-oil emulsion comprising a first oil-soluble solid sunscreen, a second oil-soluble solid sunscreen, and a non-polar silicone oil.

BACKGROUND OF THE INVENTION

The majority of highly effective sunscreens are oily or oil-soluble. These sunscreens are necessary for UV blocking, but have an unpleasant heavy, oily skin feel and present formulation difficulties such as sunscreen solubility and compatibility with other components. To counter the heavy, oily skin feel associated with sunscreen compositions, such products are commonly formulated as emulsions. The majority of such emulsions are oil-in-water emulsions wherein the aqueous phase (which in most cases is predominantly water) is thickened with polymeric thickeners. One problem with oil-in-water emulsions is that, being water-based, they too easily rinse or rub off of the skin, e.g., after perspiring, swimming, or washing hands. Considerably fewer sunscreen compositions in the form of an inverse emulsion (water-in-oil) exist. Inverse emulsions have a tendency to feel greasy and heavy. There is a desire to provide a sunscreen composition comprising a water-in-oil emulsion which has a pleasant skin feel and which does not rinse or rub off the skin too easily. To accomplish this desire, silicone oil may be incorporated into the composition as the primary oil-phase component.

With the incorporation of silicone oil into a sunscreen composition, however, other issues become critical, such as sunscreen solubility. Poor sunscreen solubility leads to the sunscreen precipitating out of the oil phase at certain concentrations or temperatures, resulting in crystals that the user can see and feel, as well as compositions with reduced or limited UV protection benefits. Generally, it is easier to solubilize liquid sunscreens in silicone oil than it is to solubilize solid sunscreens in silicone oil. For broad spectrum UV protection, it is typically necessary to use a combination of UV-A blocking sunscreens and UV-B blocking sunscreens. While effective UV-B blocking sunscreens are available in both liquid and solid form, almost all of the most effective UV-A blocking sunscreens currently approved for use are only available in solid form. A polar-oil solvent may be used to help solubilize solid UV-A blocking sunscreens, but as more solvent is added to a composition, the more greasy, heavy, and unpleasant the composition feels. There is a need to improve the solubility in silicone oil of solid UV-A blocking sunscreens without the addition of more solvent, so that even at high concentrations or temperatures the solid sunscreens do not separate out of the oil phase. Further, there is a need to provide a sunscreen composition with a pleasant skin feel and sufficient UV blocking.

SUMMARY OF THE INVENTION

The addition of more solid sunscreens to the oil phase of a water-in-oil emulsion would seem to make solubility even more difficult to achieve. But, surprisingly, it has been found that solubility is improved when more solid sunscreens are added to the oil phase. In fact, two types of solid sunscreens solubilize into the silicone oil better than one type of solid sunscreen alone. For example, in a composition comprising two solid sunscreens, oxybenzone and avobenzone, it has been found that when the amount of oxybenzone is increased, avobenzone tends to precipitate out of the silicone oil less frequently. As a result of these unexpected learnings, more oxybenzone may be used in a composition in place of a sunscreen solvent. This approach may provide higher UV-A efficacy, with better skin feel, and without crystallization issues.

In one embodiment, a personal-care composition is in the form of a water-in-oil emulsion, comprising at least about 10% of a non-polar silicone oil; from about 0.01% to about 10% of a first oil-soluble solid sunscreen; and from about 0.01% to about 10% a second oil-soluble solid sunscreen. In this embodiment, the weight ratio of the first oil-soluble solid sunscreen to the second oil-soluble solid sunscreen is from about 0.8 to about 2.0 and the first oil-soluble solid sunscreen is oxybenzone.

In another embodiment, a personal-care composition is in the form of a water-in-oil emulsion, comprising at least about 10% of a non-polar silicone oil; from about 0.1% to about 10% oxybenzone; and from about 0.1% to about 10% avobenzone. In this embodiment, the weight ratio of oxybenzone to avobenzone is from about 0.8 to about 2.0.

In a further embodiment, a personal-care composition is in the form of a water-in-oil emulsion, comprising at least about 10% of a non-polar silicone oil; from about 1% to about 6% oxybenzone; from about 1% to about 5% avobenzone; and a skin-care active selected from the group consisting of a vitamin $B_3$ compound, a sugar amine, a peptide, a hexamidine compound, and combinations thereof. In this embodiment, the weight ratio of oxybenzone to avobenzone is from about 1.0 to about 1.5.

In another embodiment, the invention relates to a method for improving the solubility of a second oil-soluble solid sunscreen in the oil phase of a water-in oil emulsion, comprising the step of: combining a first oil-soluble sunscreen and a second oil-soluble sunscreen. In this embodiment, the weight ratio of the first oil-soluble solid sunscreen to the second oil-soluble solid sunscreen is from about 1.0 to about 1.5 and the first oil-soluble solid sunscreen is oxybenzone.

In yet another embodiment, a personal-care composition comprises at least about 10% of a non-polar silicone oil; from about 0.01% to about 10% of a first oil-soluble solid sunscreen; and from about 0.01% to about 10% a second oil-soluble solid sunscreen. In this embodiment, the weight ratio of the first oil-soluble solid sunscreen to the second oil-soluble solid sunscreen is from about 0.8 to about 2.0.

In a further embodiment, a personal-care composition is in the form of a water-in-oil emulsion, comprising at least about 10% of a non-polar silicone oil; from about 0.01% to about 10% of a first oil-soluble solid sunscreen; and from about 0.01% to about 10% a second oil-soluble solid sunscreen. In this embodiment, the weight ratio of the first oil-soluble solid sunscreen to the second oil-soluble solid sunscreen is from about 0.8 to about 2.0.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION OF THE INVENTION

Figure 1:
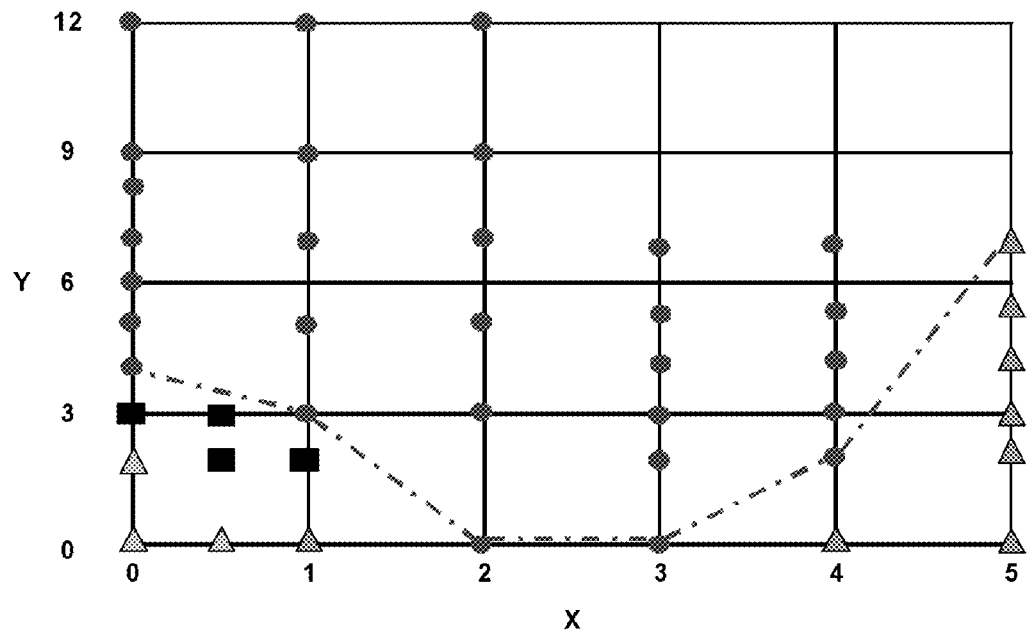
FIG. 1 is a graph of Solubility Study A results.

All percentages are by weight of the personal-care composition, unless otherwise specified. All ratios are weight ratios, unless specifically stated otherwise. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity. All ranges are inclusive and combinable; therefore, every range given throughout this specification will include every narrower range that falls within such broader range as if such narrower ranges were all expressly written herein.

"Personal-care composition," as used herein, means compositions suitable for topical application on mammalian keratinous tissue. Compositions of the present invention may be used in skin-care, cosmetic, and hair-care products; non-limiting uses of which include antiperspirants, deodorants, lotions (e.g. hand lotion and body lotion), skin-care products (e.g., face and neck lotions, serums, sprays), sunless tanners, cosmetics (e.g., foundation, concealer, blush, lipstick, lip gloss), depilatories, shampoos, conditioning shampoos, hair conditioners, hair dyes, body washes, moisturizing body washes, shower gels, skin cleansers, cleansing milks, hair and body washes, in-shower body moisturizers, pet shampoos, shaving preparations, after-shaves, razor moisturizing/lubricating strips, razor shave-gel bars, bar soaps, cleansing products, feminine-care products, oral-care products, and baby-care products.

"Keratinous tissue," as used herein, refers to keratin-containing layers disposed as the outermost protective covering of mammals which includes, but is not limited to, skin, hair, and nails.

"Soluble" and "solubility," as used herein, refer to compositions where no precipitation or crystallization of the components occurs upon storage for up to a month at temperatures ranging from −7 degrees C. to 25 degrees C.

"Derivatives," as used herein, means ester, ether, amide and/or salt derivatives of the relevant compound.

"Polar," as used herein to describe oils, means a material with a solubility parameter of greater than or equal to 7.4 $(calories/cm^3)^{0.5}$ to about 11 $(calories/cm^3)^{0.5}$. "Non-polar," as used herein, means a material with a solubility parameter of less than 7.4 $(calories/cm^3)^{0.5}$. Solubility parameters are discussed in more detail by C. D. Vaughan in "The Solubility Parameter: What is it?," Cosmetics & Toiletries vol. 106, November, 1991, pp. 69-72. Solubility parameter may be determined or calculated according to procedures discussed within Barton, AFM (1991), *Handbook of Solubility Parameters and Other Cohesion Parameters*, 2nd edition, CRC Press.

I. Personal-Care Composition

In one embodiment, the personal-care composition of the present invention is a water-in-oil emulsion. In certain embodiments, the personal-care composition may have a viscosity of from about 5,000 cps (centipoise) to about 1,000,000 cps, or from about 10,000 cps to about 500,000 cps, or from about 15,000 cps to about 200,000 cps.

In one embodiment, the personal-care composition comprises at least about 5% of an aqueous phase. In certain embodiments, the personal-care composition may comprise from about 10% to about 80%, or from about 10% to about 60%, by weight of the composition, of an aqueous phase. Within the emulsion the aqueous phase may be the internal or discontinuous phase.

The aqueous phase typically comprises water. In one embodiment, the aqueous phase may comprise only water. In other embodiments, the aqueous phase may comprise components other than water (i.e., non-water components), including but not limited to water-soluble moisturizing agents, conditioning agents, salts, anti-microbials, humectants and/or other water-soluble skin care actives, to impart an increased benefit to the keratinous tissue. In one embodiment, the aqueous phase of the personal-care composition comprises a humectant such as glycerin and/or other polyols. The aqueous phase may be substantially to totally free of water.

In one embodiment, the personal-care composition comprises at least about 15% of an oil phase. In certain embodiments, the personal-care composition comprises from about 20% to about 90%, or from about 40% to about 80%, by weight of the composition, of an oil phase. Within the emulsion, the oil phase may be the external or continuous phase.

The oil phase may comprise silicone oils, non-silicone oils such as hydrocarbon oils, esters, ethers, the like, and mixtures thereof. In a preferred embodiment, the oil phase comprises a silicone oil.

A. Non-Polar Silicone Oil

The personal-care composition may comprise a non-polar silicone oil. In certain embodiments, the non-polar silicone oil may have a solubility parameter of less than 7.4 $(calories/cm^3)^{0.5}$. In certain embodiments, the personal-care composition may comprise at least about 10%, or at least about 20%, or at least about 30%, or at least about 40%, by weight of the composition, of a non-polar silicone oil.

Non-limiting examples of suitable non-polar silicone oils include linear and cyclic polydimethylsiloxanes, including cyclomethicones (cyclotetrasiloxane, cyclopentasiloxane, cyclohexasiloxane), dimethicones, and mixtures thereof. Commercially available examples of these types of silicones include the Dow Corning 200 series, Dow Corning 344, and Dow Corning 345 (all available from Dow Corning™ Corp.); and SF1202, SF1204, and the Viscasil™ series (all available from the G.E. Silicones™). Additional non-polar silicone oils include alkyl (for example, 2 carbons to 30 carbons) and aryl (for example, phenyl or styrenyl) substituted silicones, including by not limited to phenyl methicone, phenyl dimethicone, phenyl trimethicone, diphenyl dimethicone, phenylethyl dimethicone, hexyl dimethicone, lauryl dimethicone, cetyl dimethicone, stearyl dimethicone, bis-stearyl dimethicone, and mixtures thereof. In one embodiment, the non-polar silicone oil is low viscosity, meaning a viscosity less than 50 cst.

B. Oil-Soluble Solid Sunscreens

The personal-care composition may comprise at least two oil-soluble solid sunscreens. "Oil-soluble solid sunscreen," as used herein, means a sunscreen which is, in its commercially-available purified form, a crystalline and/or solid compound having the potential to solubilize in polar oils. In one embodiment, the oil-soluble solid sunscreen may have a solubility parameter of from about 7.4 $(calories/cm^3)^{0.5}$ to about 11 $(calories/cm^3)^{0.5}$. To provide maximum UV protection, it is preferred that the oil-soluble solid sunscreen be substantially dissolved—and thus not remain in a solid form—in the final personal-care composition.

Suitable oil-soluble solid sunscreens include, but are not limited to, avobenzone (butyl methoxydibenzoylmethane; commercially available as Parsol 1789 from DSM Nutritional Products, Inc.), oxybenzone (benzophenone-3; commercially available as Neo Heliopan BB from Symrise), and bemotrizinol (bis-ethylhexyloxyphenol methoxyphenyl triazine; commercially available as Tinosorb S from Ciba Corp.), diethylamino hydroxybenzoyl hexyl benzoate (commercially available as Uvinul A Plus from BASF), ethylhexyl triazone (commercially available as Uvinul T150 from BASF), 4-methylbenzylidene camphor (commercially available as Parsol 5000 from DSM Nutritional Products, Inc.), and derivatives and mixtures thereof. Additional non-limiting examples of suitable oil-soluble solid sunscreens are disclosed in The Cosmetic, Toiletry, and Fragrance Association's *The International Cosmetic Ingredient Dictionary and Handbook*, 10$^{th}$ Ed., Gottschalck, T. E. and McEwen, Jr., Eds. (2004), p. 2267 and pp. 2292-93.

In certain embodiments, the personal-care composition comprises from about 0.1% to about 10%, or from about 1% to about 6%, or from about 1.5% to about 4%, by weight of the composition, of a first oil-soluble solid sunscreen. In particular embodiments, the first oil-soluble solid sunscreen is a UV-B blocking sunscreen. In other embodiments, the first oil-soluble solid sunscreen is a UV-A blocking sunscreen. An exemplary first oil-soluble solid sunscreen is oxybenzone. In certain embodiments, the personal-care composition comprises from about 0.1% to about 10%, or from about 1% to about 5%, or from about 1.5% to about 3%, by weight of the composition, of a second oil-soluble solid sunscreen. In particular embodiments, the second oil-soluble solid sunscreen is a UV-A blocking sunscreen. An exemplary second oil-soluble solid sunscreen is avobenzone.

Surprisingly, it has been found that within a specified weight ratio of a first oil-soluble solid sunscreen to a second oil-soluble solid sunscreen, the addition of the first oil-soluble solid sunscreen improves the solubility of the second oil-soluble solid sunscreen. This is believed to run counter to what is known in the art of solubility—adding more solid sunscreen would seem to worsen solubility. Indeed, if the weight ratio of the first oil-soluble solid sunscreen to the second oil-soluble solid sunscreen outside the specified weight ratio, the second oil-soluble solid sunscreen will precipitate out or crystallize. In certain embodiments, the weight ratio of the first oil-soluble solid sunscreen to the second oil-soluble solid sunscreen is from about 0.8 to about 2.0, or from about 1.0 to about 1.5, or from about 1.2 to about 1.4.

C. Polar Oil

The personal-care composition may comprise a polar oil. In certain embodiments, the composition may comprise greater than about 2%, or greater than about 5%, or greater than about 10%, by weight of the composition, of polar oil. In some embodiments, the polar oil may have a solubility parameter of from about 7.4 (calories/cm$^3$)$^{0.5}$ to about 11 (calories/cm$^3$)$^{0.5}$.

Suitable polar oils include ethers, esters, amides, propoxylates, and mixtures thereof. The aforementioned oils may be saturated, unsaturated, aliphatic (straight or branched chains), alicyclic, or aromatic.

Suitable non-sunscreen polar oils include, but are not limited to, butyl and isopropyl phthalimide (Pelemol™ BIP), phenylethyl benzoate (X-tend™ 226), dicaprylyl carbonate (Tegosoft™ DEC), isopropyl lauroyl sarcosinate (Eldew™ SL 205), butyl octylsalicylate (Hallbrite™ BHB), dioctyl malate, dicaprylyl maleate (Hallbrite™ DCM), di-isopropyl adipate, dibutyl adipate (Cetiol B), isononyl isononanoate, isopropyl isostearate, propylene glycol dicaprate, C12-15 alcohol benzoate (Finsolv TN), PPG-11 stearyl ether, and derivatives and mixtures thereof. In certain embodiments, the composition may comprise no more than about 10%, or no more than about 5%, or no more than about 2%, by weight of the composition, of a non-sunscreen polar oil.

Suitable sunscreen polar oils include, but are not limited to, ethylhexyl methoxy-cinnamate (octinoxate), ethylhexyl salicylate (octisalate), octocrylene, homosalate, menthyl anthranilate (meradimate), and mixtures thereof. To be considered a polar oil, a sunscreen should be in liquid form. In one embodiment, the composition comprises more than one sunscreen polar oil.

D. Non-Emulsifying Silicone Elastomer

The personal-care composition may comprise a non-emulsifying silicone elastomer. "Non-emulsifying silicone elastomer" means that the silicone elastomer comprises no polyoxyalkylene groups. Typically, these non-emulsifying silicone elastomers are supplied swollen in and/or blended with non-polar silicone oils.

Suitable non-emulsifying silicone elastomers include the CTFA (Cosmetic, Toiletry, and Fragrance Association *International Cosmetic Ingredient Dictionary and Handbook*, 11$^{th}$ ed.) designated dimethicone/vinyl dimethicone crosspolymers such as supplied by General Electric™ (SFE 839), and Shin Etsu™ (KSG 15 and 16), and dimethicone/phenyl vinyl dimethicone crosspolymer such as KSG 18 available from Shin Etsu™. Other exemplary silicone elastomers include the CTFA designated dimethicone crosspolymers including Dow Corning™ (DC 9040, DC 9041, DC 9045).

E. Emulsifier

The personal-care composition may comprise one or more emulsifiers that may be linear, branched, and/or cross-linked. In certain embodiments, the personal-care composition may comprise from about 0.05% to about 20%, or from about 0.1% to about 10%, by weight of the composition, of total emulsifier. Non-limiting examples of emulsifiers are disclosed in U.S. Pat. No. 3,755,560, U.S. Pat. No. 4,421,769, and *McCutcheon's Detergents and Emulsifiers*, North American Edition and International Edition, pages 235-246 (1993).

Emulsifiers may include emulsifying silicone elastomers. Suitable emulsifying silicone elastomers include cross-linked organopolysiloxane elastomers having at least one polyalkyl ether or polyglycerolated unit. These cross-linked elastomers may also be co-modified to include alkyl substituents. Particularly useful emulsifying polyoxyethylene cross-linked elastomers include Shin Etsu's KSG-21, KSG-210, KSG-24, KSG-240, KSG-31, KSG-310, KSG-32, KSG-320, KSG-33, KSG-330, KSG-34, and KSG-340.

Linear or branched type silicone emulsifiers are also useful in this application. Particularly useful polyether modified elastomers include Shin Etsu's KF-6011, KF-6012, KF-6013, KF-6015, KF-6016, KF-6017, KF-6043, KF-6028, and KF-6038.

F. Optional Ingredients

1. Particulate Material

In particular embodiments, the personal-care composition comprises from about 0.1% to about 40%, or from about 1% to about 30%, or from about 5% to about 20%, by weight of the composition, of one or more particulate materials. Non-limiting examples of suitable powders include inorganic powders (e.g., iron oxides, titanium dioxides, zinc oxides, silica), organic powders, composite powders, optical brightener particles, and mixtures of any of the foregoing. These particulates can, for instance, be platelet shaped, spherical, elongated or needle-shaped, or irregularly shaped; surface coated or uncoated; porous or non-porous; charged or uncharged; and can be added to the current compositions as a powder or as a pre-dispersion. In one embodiment, the particulate material is hydrophobically coated.

Suitable organic powder particulate materials include, but are not limited, to polymeric particles chosen from the methylsilsesquioxane resin microspheres, e.g., Tospearl™ 145A, (Toshiba Silicone); microspheres of polymethylmethacrylates, e.g., Micropearl™ M 100 (Seppic); the spherical particles of crosslinked polydimethylsiloxanes, e.g., Trefil™ E 506C or Trefil™ E 505C (Dow Corning Toray Silicone); spherical particles of polyamide, e.g., nylon-12, and Orgasol™ 2002D Nat C05 (Atochem); polystyrene microspheres, e.g., Dyno Particles, sold under the name Dynospheres™, and ethylene acrylate copolymer, sold under the name FloBead™ EA209 (Kobo); aluminum starch octenylsuccinate, e.g., Dry Flo™ (National Starch); polyethylene particulates, e.g., Microthene™ FN510-00 (Equistar) and Micropoly® 220L (Micro Powders, Inc.); microspheres of polypropylene, e.g., Mattewax™ 511 (Micro Powders, Inc.); silicone resin; platelet shaped powder made from L-lauroyl lysine; and mixtures thereof.

In one embodiment, the composition comprises interference pigments, including hydrophobically-modified interference pigments. Herein, "interference pigments" means thin, plate-like layered particles having two or more layers of controlled thickness. The layers have different refractive indices that yield a characteristic reflected color from the interference of typically two, but occasionally more, light reflections, from different layers of the plate-like particle. One example of interference pigments are micas layered with about 50-300 nm films of $TiO_2$, $Fe_2O_3$, silica, tin oxide, and/or $Cr_2O_3$ and include pearlescent pigments. Interference pigments are available commercially from a wide variety of suppliers, for example, Rona (Timiron™ and Dichrona™), Presperse (Flonac™), Englehard (Duochrome™), Kobo (Interfine, Interval, SK-45-R, and SK-45-G), BASF (Sicopearls™) and Eckart (Prestige™). In one embodiment, the average diameter of the longest side of the individual particles of interference pigments is less than about 75 microns, and alternatively less than about 50 microns.

Particulates may also include colorants. Non-limiting examples of suitable colorants include iron oxides, ferric ammonium ferrocyanide, manganese violet, ultramarine blue, and chromium oxide, phthalocyanine blue and green pigment, encapsulated dyes, inorganic white pigments, for example $TiO_2$, $ZnO$, or $ZrO_2$, and mixtures thereof.

2. Insoluble Sunscreens

In one embodiment, the personal-care composition comprises from about 0.001% to about 10%, or from about 0.1% to about 5%, by weight of the composition, of an insoluble sunscreen. Non-limiting examples of suitable insoluble sunscreens include methylene bis-benzotriazolyl tetramethylbutyl-phenol (Tinosorb M), titanium dioxides, zinc cerium oxides, zinc oxides, and derivatives and mixtures thereof.

3. Skin-Care Actives

Certain embodiments of the personal-care composition comprise one or more skin-care actives. Suitable skin-care actives include, but are not limited to, vitamins, peptides, sugar amines, oil control agents, tanning actives, anti-acne actives, desquamation actives, anti-cellulite actives, chelating agents, skin lightening agents, flavonoids, protease inhibitors, non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobials, and antifungals. These skin-care actives and others are provided in further detail in U.S. Application Publication Nos. US2006/0275237A1, US2004/0175347A1, and US2006/0263309A1.

Particularly suitable skin-care actives include a vitamin $B_3$ compound, a sugar amine, a peptide, a hexamidine compound, and combinations thereof. As used herein, "vitamin $B_3$ compound" means a compound having the formula:

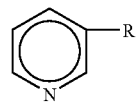

wherein R is —$CONH_2$ (i.e., niacinamide), —COOH (i.e., nicotinic acid) or —$CH_2OH$ (i.e., nicotinyl alcohol); derivatives thereof; and salts of any of the foregoing. As used herein, "sugar amine" includes isomers and tautomers of such and its salts (e.g., HCl salt) and its derivatives. Examples of sugar amines include glucosamine, N-acetyl glucosamine, mannosamine, N-acetyl mannosamine, galactosamine, N-acetyl galactosamine, their isomers (e.g., stereoisomers), and their salts (e.g., HCl salt). As used herein, "peptide" refers to peptides containing ten or fewer amino acids and their derivatives, isomers, and complexes with other species such as metal ions (e.g., copper, zinc, manganese, magnesium, and the like). As used herein, "hexamidine compound" means a compound having the formula:

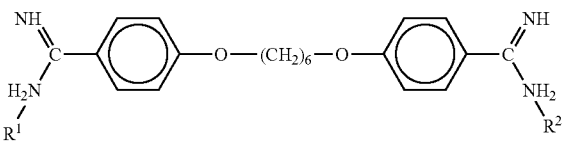

wherein $R^1$ and $R^2$ are optional or are organic acids (e.g., sulfonic acids, etc.), and its salts and derivatives.

Further suitable skin-care actives include white tea extract, green tea extract, ginseng, and other natural or botanical compounds.

4. Additional Optional Ingredients

In particular embodiments, the composition of the present invention may comprise a wide range of additional ingredients. The CTFA (Cosmetic, Toiletry, and Fragrance Association *International Cosmetic Ingredient Dictionary and Handbook*, 11th ed.) describes a wide variety of non-limiting cosmetic and pharmaceutical ingredients commonly used in the skin care industry, which are available for use in the present invention. Exemplary functional classes include, but are not limited to, abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, emollients, external analgesics, film formers or materials, opacifying agents, pH adjusters, propellants, reducing agents, sequestrants, skin bleaching and lightening agents, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives. In one embodiment, the composition of the present invention may comprise non-polar hydrocarbon oils. Non-limiting examples of suitable non-polar hydrocarbon oils include mineral oils and branched chain hydrocarbons (e.g. Permethyl™ (Permethyl Corporation™) and Isopar™ (Exxon™)).

II. Methods

The present invention further relates to a method of improving the solubility of oil-soluble solid sunscreens in the oil phase of a water-in-oil emulsion. In one embodiment, the solubility of a second oil-soluble solid sunscreen in the oil phase of a water-in oil emulsion is improved by combining a first oil-soluble sunscreen and a second oil-soluble sunscreen, wherein the weight ratio of the first oil-soluble solid sunscreen to the second oil-soluble solid sunscreen is from about 1.0 to about 1.5. In a particular embodiment, the first oil-soluble solid sunscreen is oxybenzone and the second oil-soluble solid sunscreen is avobenzone.

The present invention further relates to methods of protecting keratinous tissue from the harmful effects of UV radiation by the application of any of the aforementioned personal-care compositions to keratinous tissue. Such methods generally involve attenuating or reducing the amount of UV radiation which reaches the keratinous tissue. In certain embodiments, the personal-care compositions described herein are suitable for use as a sunscreen to provide protection to keratinous tissue from the harmful effects of UV radiation such as sunburn, dry or damaged hair, and premature aging of the skin.

In a further aspect, the personal-care composition may be used to improve or regulate the condition of keratinous tissue. Conditions to be improved or regulated include increasing the luminosity or "glow" of the skin, reducing the appearance of wrinkles and coarse deep lines, fine lines, crevices, bumps, and large pores; thickening of keratinous tissue (e.g., building the epidermis and/or dermis and/or sub-dermal layers of the skin, and where applicable the keratinous layers of the nail and hair shaft, to reduce skin, hair, or nail atrophy); increasing the convolution of the dermal-epidermal border (also known as the rete ridges); preventing loss of skin or hair elasticity, for example, due to loss, damage and/or inactivation of functional skin elastin, resulting in such conditions as elastosis, sagging, loss of skin or hair recoil from deformation; reduction in cellulite; change in coloration to the skin, hair, or nails, for example, under-eye circles, blotchiness (e.g., uneven red coloration due to, for example, rosacea), sallowness, discoloration caused by telangiectasia or spider vessels, dryness, brittleness, and graying hair.

III. Examples

The following describe non-limiting examples of the personal-care composition. The reported percentages indicate the weight of the component expressed as a percentage of the total weight of the personal-care composition. Each Example may comprise one or more of the optional ingredients in amounts as disclosed herein. The Examples may be prepared as follows.

In a suitable vessel, combine the aqueous-phase ingredients and heat to 90° C. with gentle mixing. In a separate vessel, combine the sunscreens (e.g., octisalate, homosalate, octocrylene, avobenzone, oxybenzone), polar oil (e.g., isopropyl lauroyl sarcosinate), and wax (e.g., Cirebelle 303, Accumelt 72, Accumelt 82, or Accumelt 90) and heat to 90° C. with mixing. When both solutions are translucent and free of particulates to the naked eye, pour the hot water phase into the sunscreen mixture, then immediately add the remaining silicone phase ingredients to the same container. Stir vigorously until smooth and homogeneous while maintaining the temperature of the product above the wax melt point. Remove the product from the heat source and cool to 33° C. with constant stirring. Scrape the sides of the container frequently to ensure the product is sheared homogeneously. Pour product into suitable containers.

Alternatively, the product can be prepared without shear during cooling. In this case, upon removal from the heat source, the hot emulsion is immediately poured into suitable containers and allowed to come to room temperature.

| Ingredients | Ex. 1 | Ex. 2 | Ex. 3 | Ex. 4 | Ex. 5 |
|---|---|---|---|---|---|
| Oil Phase | | | | | |
| Octisalate | 5.00 | 5.00 | 5.00 | 5.00 | 5.00 |
| Homosalate | 3.50 | 10.00 | 10.00 | 10.00 | 10.00 |
| Octocrylene | 1.30 | 1.30 | 1.70 | 2.60 | 2.60 |
| Avobenzone | 1.50 | 1.50 | 2.00 | 3.00 | 3.00 |
| Oxybenzone | 1.50 | 2.50 | 2.50 | 4.00 | 4.00 |
| Isopropyl Lauroyl Sarcosinate | 3.00 | 3.00 | — | 2.00 | 4.00 |
| Dow Corning ™ 9045[1] | qs | 47.55 | 46.05 | 41.65 | 25.75 |
| KSG-310[2] | 3.00 | 3.00 | 3.00 | 3.00 | 3.00 |
| Tospearl ™ 145A[3] | 16.00 | 6.00 | 6.00 | 6.00 | 6.00 |
| Mattewax 511[4] | 4.00 | — | — | — | 4.00 |
| Micropoly 220L[5] | — | 4.00 | 4.00 | 4.00 | — |
| Cab-O-Sil T720[6] | 0.10 | — | — | — | — |
| Dry Flow PC[7] | 1.00 | — | — | — | — |
| Cirebelle 303[8] | 5.00 | — | — | — | — |
| Accumelt 72[9] | — | — | 7.00 | — | — |
| Accumelt 82[9] | — | — | — | 5.00 | — |
| Accumelt 90[9] | — | 3.00 | — | — | 5.00 |
| KF-6105[10] | — | 0.50 | 0.50 | 0.50 | 0.50 |
| KF-6038[11] | 0.50 | — | — | — | — |
| Perfume | 0.25 | 0.15 | 0.25 | 0.25 | 0.15 |
| Aqueous Phase | | | | | |
| Propylene Glycol | — | 3.20 | 3.20 | 3.20 | 3.20 |
| Purified Water | — | qs | qs | qs | qs |
| Glycerin | — | 2.00 | 2.00 | 2.00 | 2.00 |
| White Tea Extract[12] | — | 1.00 | 1.00 | 1.00 | 1.00 |
| Ginseng[13] | — | 0.50 | 0.50 | 0.50 | 0.50 |
| Niacinamide | — | 2.00 | 2.00 | 2.00 | 2.00 |
| Palestrina[14] | — | 0.58 | 0.58 | 0.58 | 0.58 |
| Panthenol | — | 0.20 | 0.22 | 0.22 | 0.25 |
| Hexamidine diisethionate | — | 0.10 | 0.10 | 0.10 | 0.10 |
| Disodium EDTA | — | 0.01 | 0.01 | 0.01 | 0.01 |
| Total | 100.00 | 100.00 | 100.00 | 100.00 | 100.00 |

[1]Dimethicone Crosspolymer (about 12%) and Cyclopentasiloxane (about 88%) from Dow Corning ™, Midland, MI.
[2]PEG-15/Lauryl Dimethicone Crosspolymer and Mineral Oil from Shin-Etsu ™, Newark, CA.
[3]Polymethylsilsesquioxane from Momentive ™ Performance Materials, Inc., Albany, NY.
[4]Polypropylene from Micro Powders, Inc., Tarrytown, NY.
[5]Polyethylene from Micro Powders, Inc., Tarrytown, NY.
[6]Fumed Silica from Cabot Corp.
[7]Dry-Flo PC from National Starch & Chemical Company, Bridgewater, NJ.
[8]Polyethylene Wax from Arch Chemicals, Inc., South Plainfield, NJ.
[9]Synthetic Wax from The International Group Inc., Toronto, Ontario.
[10]Lauryl Polyglyceryl-3 Polydimethylsiloxyethyl Dimethicone from Shin-Etsu ™, Newark, CA.
[11]Lauryl PEG-9 Polydimethylsiloxyethyl Dimethicone from Shin-Etsu ™, Newark, CA.
[12]White Tea Extract from Carrubba, Inc., Milford, CT.
[13]Ginseng from Symrise, Teterboro, NJ.
[14]Anti-aging peptide solution from Sederma, Inc., Edison, NJ.

IV. Comparative Examples

The following two solubility studies demonstrate the unexpected improvement in solubility from the claimed combinations of two oil-soluble solid sunscreens. For these solubility studies, the oil phase of a water-in-oil emulsion was created by combining ingredients in a suitable vessel, heating to 90° C. with mixing, and then cooling to room temperature while mixing. The oil-phase composition for each study, shown in the table below, consists of a combination of the non-polar silicone oil, mineral oil, liquid-sunscreen actives, the oil-soluble solid sunscreen avobenzone, and varying levels of the polar oil isopropyl lauroyl sarcosinate and the oil-soluble solid sunscreen oxybenzone.

| Type of Material | Material | Parts by weight | |
|---|---|---|---|
| | | Study A | Study B |
| Non-polar Silicone Oil | Cyclopentasiloxane | 44.0 | 44.0 |
| Emollient | Mineral Oil | 2.1 | 2.1 |
| Liquid Sunscreen | Homosalate | 9.0 | 9.0 |
| Liquid Sunscreen | Octisalate | 4.5 | 4.5 |
| Liquid Sunscreen | Octocrylene | 1.7 | 1.7 |
| Oil-soluble Solid Sunscreen | Avobenzone | 2.0 | 3.0 |
| Oil-soluble Solid Sunscreen | Oxybenzone | 0.0-5.0 | 0.0-5.0 |
| Polar Oil | Isopropyl Lauroyl Sarcosinate | 0.0-12.0 | 0.0-12.0 |

Once each of the oil phases in the above studies were at room temperature, they were filled into glass vials and stored at three different conditions: room temperature (RT; approximately 22° C.), 5° C., and −7° C. After about one month of storage, all vials were equilibrated at room temperature and then visually examined for any signs of crystallization or precipitation of the oil-soluble solid sunscreens.

Figure 2:
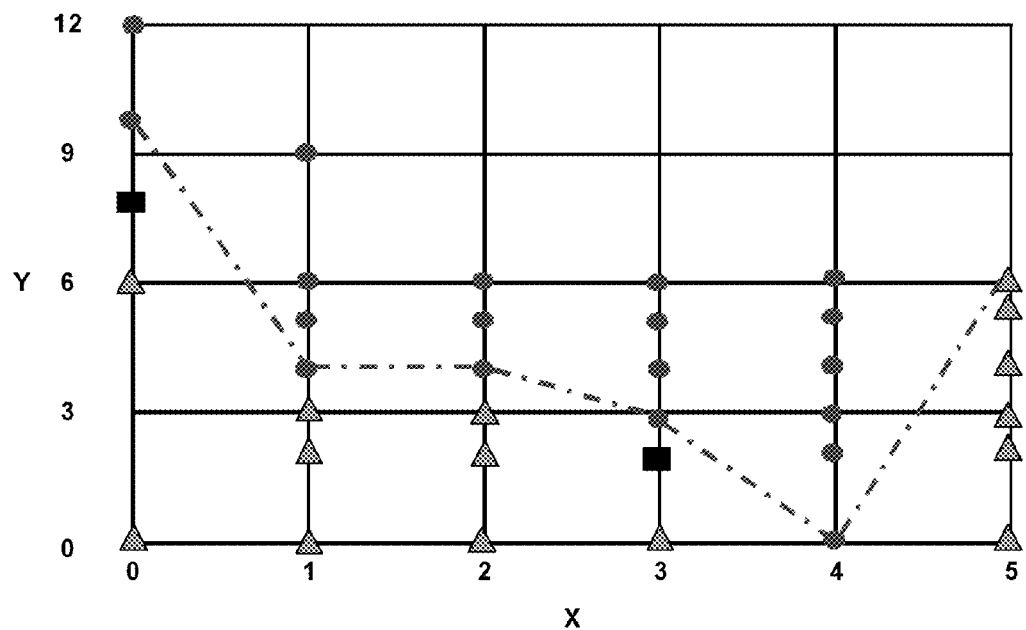
FIG. 2 is a graph of Solubility Study B results.

The results of the two solubility studies are provided in FIG. 1, describing solubility Study A results (2% avobenzone), and FIG. 2, describing solubility Study B results (3% avobenzone). The x-axes, X, represent the % oxybenzone, i.e., from 0% to 5% oxybenzone. The y-axes, Y, represent the % isopropyl lauroyl sarcosinate, i.e., from 0% to 12% isopropyl lauroyl sarcosinate. The circle data plot means soluble under all test conditions (RT, 5° C., and −7° C.). The square data plot means borderline soluble (one or a few crystals only at −7° C.). The triangle data plot means not soluble at one or more test conditions. FIGS. 1 and 2 show the unexpected improvement in avobenzone solubility when oxybenzone is added at oxybenzone to avobenzone ratios of between 0.8 and 2.0, with maximum solubility at a ratio between 1 and 1.5. On or above the dashed line, the avobenzone is fully solubilized. Below the dashed line, the avobenzone is borderline soluble or not soluble at all. FIGS. 1 and 2 illustrate that with no oxybenzone present, significant levels of the non-sunscreen polar oil isopropyl lauroyl sarcosinate are required to keep avobenzone soluble in the oil phase. Specifically, FIG. 1 shows that with no oxybenzone present, greater than about 4% isopropyl lauroyl sarcosinate is required to keep avobenzone soluble in the oil phase; FIG. 2 shows that with no oxybenzone present, greater than about 10% isopropyl lauroyl sarcosinate is required to keep avobenzone soluble in the oil phase. However, as low levels of the oil-soluble solid sunscreen oxybenzone are added, less polar oil is required to keep the sunscreens soluble. Finally, as even higher levels of oxybenzone are added, solubility of the sunscreens then becomes poorer again. The figures demonstrate the unexpected solubility benefit within a specified weight ratio range of the first oil-soluble solid sunscreen, oxybenzone, to the second oil-soluble solid sunscreen, avobenzone. Surprisingly, the addition of more of the first oil-soluble solid sunscreen improves the solubility of the second oil-soluble solid sunscreen.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal-care composition in the form of a water-in-oil emulsion comprising:
   a) at least about 10% of a non-polar silicone oil;
   b) from about 0.1% to about 10% oxybenzone; and
   c) from about 1% to about 5% avobenzone;
   wherein the weight ratio of oxybenzone to avobenzone is from 1.0 to 1.5.

2. The personal-care composition of claim 1, wherein the non-polar silicone oil is selected from the group consisting of cyclomethicone, dimethicone, and mixtures thereof.

3. The personal-care composition of claim 1, comprising at least about 20% of a non-polar silicone oil.

4. The personal-care composition of claim 1, comprising at least about 30% of a non-polar silicone oil.

5. The personal-care composition of claim 1, comprising at least about 40% of a non-polar silicone oil.

6. The personal-care composition of claim 1, comprising from about 1% to about 6% oxybenzone.

7. The personal-care composition of claim 1, wherein the weight ratio of oxybenzone to avobenzone is from about 1.2 to about 1.4.

8. The personal-care composition of claim 1, further comprising a skin-care active, wherein the skin-care active is selected from the group consisting of vitamins, peptides, sugar amines, oil control agents, tanning actives, anti-acne actives, desquamation actives, anti-cellulite actives, chelating agents, skin lightening agents, flavonoids, protease inhibitors, non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobials, antifungals, and mixtures thereof.

9. The personal-care composition of claim 1, further comprising a skin-care active, wherein the skin-care active is selected from the group consisting of a vitamin $B_3$ compound, a sugar amine, a peptide, a hexamidine compound, and combinations thereof.

10. A personal-care composition in the form of a water-in-oil emulsion comprising:
   a) at least about 10% of a non-polar silicone oil;
   b) from about 1% to about 6% oxybenzone;
   c) from about 1% to about 5% avobenzone; and
   d) a skin-care active selected from the group consisting of a vitamin $B_3$ compound, a sugar amine, a peptide, a hexamidine compound, and combinations thereof;
   wherein the weight ratio of oxybenzone to avobenzone is from 1.0 to 1.5.

11. A method for improving the solubility of avobenzone in the oil phase of a water-in oil emulsion, comprising the step of: combining from about 0.1% to about 10% oxybenzone, from about 1% to about 5% avobenzone and at least 10% of a non-polar silicone oil; wherein the weight ratio of the oxybenzone to avobenzone is from 1.0 to 1.5.

12. A personal-care composition comprising an aqueous phase and an oil phase, wherein the aqueous phase comprises at least 5% water and the oil phase comprises:
   a) at least about 10% of a non-polar silicone oil;
   b) from about 0.1% to about 10% oxybenzone; and
   c) from about 1% to about 5% avobenzone;
   wherein the weight ratio of oxybenzone to avobenzone is from 1.0 to 1.5.

* * * * *